(12) United States Patent
Ohashi

(10) Patent No.: US 9,250,201 B2
(45) Date of Patent: Feb. 2, 2016

(54) X-RAY ANALYZER

(71) Applicant: HORIBA, Ltd., Kyoto (JP)

(72) Inventor: Satoshi Ohashi, Kyoto (JP)

(73) Assignee: HORIBA, LTD. (JP)

( * ) Notice: Subject to any disclaimer, the term of this patent is extended or adjusted under 35 U.S.C. 154(b) by 0 days.

(21) Appl. No.: 14/359,436

(22) PCT Filed: Dec. 5, 2012

(86) PCT No.: PCT/JP2012/081437
§ 371 (c)(1),
(2) Date: May 20, 2014

(87) PCT Pub. No.: WO2013/084905
PCT Pub. Date: Jun. 13, 2013

(65) Prior Publication Data
US 2015/0083909 A1 Mar. 26, 2015

(30) Foreign Application Priority Data
Dec. 9, 2011 (JP) .................................. 2011-270690

(51) Int. Cl.
*G01N 23/223* (2006.01)
*G01N 23/225* (2006.01)

(52) U.S. Cl.
CPC .......... *G01N 23/223* (2013.01); *G01N 23/2252* (2013.01); *G01N 2223/076* (2013.01); *G01N 2223/402* (2013.01); *G01N 2223/418* (2013.01)

(58) Field of Classification Search
USPC .......................................... 250/310; 378/82
See application file for complete search history.

(56) References Cited

U.S. PATENT DOCUMENTS

| 5,408,098 | A | * | 4/1995 | Wells ............................ 250/310 |
| 5,578,823 | A | * | 11/1996 | Taniguchi ............... H01J 37/28 250/305 |
| 6,909,770 | B2 | * | 6/2005 | Schramm et al. ............... 378/45 |
| 7,928,376 | B2 | * | 4/2011 | Kaji ..................... H01J 37/256 250/305 |

(Continued)

FOREIGN PATENT DOCUMENTS

JP 3654551 B2 3/2005
JP 2009-250867 A 10/2009

(Continued)

OTHER PUBLICATIONS

International Search Report for International Application No. PCT/JP2012/081437; date of mailing: Feb. 19, 2013, with English translation.

*Primary Examiner* — Phillip A Johnston
*Assistant Examiner* — Hsien Tsai
(74) *Attorney, Agent, or Firm* — Cantor Colburn LLP

(57) ABSTRACT

The X-ray analyzer generates a spectrum of X-rays obtained from an area on a sample where the intensity of X-rays whose energy is not included in an already set-up ROI is high and then, from the generated spectrum, identifies a new element for which an ROI is not set up. Further, the X-ray analyzer sets an ROI corresponding to the identified element and then obtains element distribution. The X-ray analyzer repeats generation of an X-ray spectrum, identification of an element, setting of an ROI, and obtaining element distribution. This avoids unintended omission of setting of an ROI and hence permits as-much-as-possible coverage of the elements in the sample. Further, distribution of a trace element is allowed to be obtained rapidly.

11 Claims, 9 Drawing Sheets

(56) References Cited

U.S. PATENT DOCUMENTS

2003/0223536 A1* 12/2003 Yun et al. .................. 378/45
2011/0144922 A1* 6/2011 Corbett et al. .............. 702/28

FOREIGN PATENT DOCUMENTS

| | | |
|---|---|---|
| JP | 2010-164442 A | 7/2010 |
| JP | 2011-38939 A | 2/2011 |

* cited by examiner

X-RAY ANALYZER

CROSS REFERENCE TO RELATED APPLICATIONS

This is the U.S. national stage of application No PCT/JP2012/081437 filed on Dec. 5, 2012. Priority under 35 U.S.C. §119(a) and 35 U.S.C. §365(b) is claimed from Japanese Application No. 2011-270690, filed on Dec. 9, 2011, the disclosure of which is also incorporated herein by reference.

BACKGROUND

1. Technical Field

The present invention relates to an X-ray analyzer scanning a sample with a beam, then detecting X-rays generated on the sample, and thereby obtaining element distribution in the sample.

2. Description of Related Art

X-ray analysis is a technique of analysis in which a beam of electron rays, X-rays, or the like is projected onto a sample, then characteristic X-rays or X-ray fluorescence generated on the sample are detected, and then from a spectrum of characteristic X-rays or X-ray fluorescence, qualitative analysis or quantitative analysis of an element contained in the sample is performed. Further, when the characteristic X-rays or the X-ray fluorescence are detected with scanning the sample with the beam, distribution of the element contained in the sample is obtained. The X-ray analyzer employing an electron beam is incorporated in an electron microscope in some cases. Japanese Patent Publication No. 3654551 discloses an example of a technique of generating element distribution image by X-ray analysis.

In the conventional art, when element distribution is to be obtained, an ROI (region of interest) is set up which is an energy range of characteristic X-rays or X-ray fluorescence corresponding to a particular element. Then, intensity distribution of characteristic X-rays or X-ray fluorescence whose energy is included in the ROI is acquired so that distribution of each element is acquired. Further, when distribution of a trace element inhomogeneously distributed on a sample is to be obtained, positioning of an area where the trace element is inhomogeneously distributed has been performed on the basis of an image other than an element distribution image, like an electron microscope image and an optical microscope image of the sample.

SUMMARY OF THE INVENTION

In a conventional method, element distribution is obtained after an ROI is set up in advance. Thus, element distribution cannot be acquired for an element for which an ROI is not set up. An ROI is allowed to be set up manually after the spectrum of characteristic X-rays or X-ray fluorescence is checked. Nevertheless, it is difficult to find a signal of a trace element from the spectrum. Thus, it is difficult to acquire element distribution of a trace element. Further, in a method of positioning based on an image other than an element distribution image, the work of generating an image other than an element distribution image, performing the positioning on the basis of the image, generating a spectrum, and checking the spectrum need be repeated until a trace element is found. This has caused a problem of time and effort. Further, the contents of obtained information are different between an element distribution image and an image other than an element distribution image. Thus, it is not ensured that an area where a trace element is inhomogeneously distributed is allowed to be identified on the basis of an image other than an element distribution image. Accordingly, in the conventional method, it is difficult to rapidly obtain element distribution covering the entire elements contained in the sample.

The present invention has been devised in view of such situations. An object thereof is to provide an X-ray analyzer that repeats setting of an ROI and identification of an element on the basis of characteristic X-rays or X-ray fluorescence whose intensity is high in the outside of the ROI and that thereby rapidly obtains element distribution covering as much as possible the elements contained in a sample.

An X-ray analyzer according to the present invention is characterized by comprising: a scanning unit for scanning a sample with a beam; an X-ray detector for detecting X-rays generated on the sample by the scanning; an element distribution obtaining unit for, from the detection result of the X-rays generated in an area on the sample scanned with the beam, obtaining intensity distribution of the X-rays whose energy or wavelength is included in a range of energy or wavelength set up in correspondence to an element contained in the sample and thereby obtaining distribution of the element; an intensity distribution acquiring unit for acquiring intensity distribution of X-rays whose energy or wavelength is not included in the range; a spectrum generating unit for generating a spectrum of X-rays generated in an area on the sample corresponding to a portion where the intensity of X-rays is not less than a predetermined intensity in the acquired intensity distribution; an element identification unit for identifying an element contained in the sample on the basis of a peak included in the generated spectrum; and a setting unit for setting a range of energy or wavelength of X-rays corresponding to the identified element, wherein the element distribution obtaining unit obtains distribution of the element identified by the element identification means, in accordance with the range set by the setting means.

In the present invention, the X-ray analyzer obtains element distribution by using a range of energy or wavelength having been set up, then generates a spectrum of X-rays obtained from an area on the sample where the intensity of X-rays whose energy or wavelength is not included in the already set-up range is high, and then identifies a new element from the generated spectrum. Further, the X-ray analyzer sets a range of energy or wavelength corresponding to the identified element and then obtains element distribution by using the set-up range. As such, the X-ray analyzer repeats generation of an X-ray spectrum, identification of an element, setting of a range of energy or wavelength, and obtaining element distribution.

The X-ray analyzer according to the present invention is characterized by further comprising a display unit for displaying an image representing the distribution of the element at each time that the element distribution obtaining unit obtains the distribution.

In the present invention, at each time of obtaining element distribution, the X-ray analyzer displays an element distribution image representing element distribution and then the user checks the distribution of each element contained in the sample.

The X-ray analyzer according to the present invention is characterized by further comprising an area specifying unit for specifying an area on the sample corresponding to the portion where the intensity of X-rays is not less than a predetermined intensity in the intensity distribution acquired by the intensity distribution acquiring unit, wherein the scanning unit scans the area specified by the area specifying unit with the beam, the X-ray detector detects X-rays generated on the area scanned with the beam, and the spectrum generating unit generates a spectrum of X-rays generated on the area on the basis of the detection result of the X-rays by the X-ray detector.

The X-ray analyzer according to the present invention is characterized in that the spectrum generating unit generates a spectrum of X-rays whose energy or wavelength is not included in the already set range of energy or wavelength.

The X-ray analyzer according to the present invention is characterized in that the element distribution obtaining unit, the intensity distribution acquiring unit, the spectrum generating unit, the element identification unit and the setting unit operates repetitively until distributions of elements of a predetermined number are obtained.

The X-ray analyzer according to the present invention is characterized in that the beam is an electron beam.

The X-ray analyzer according to the present invention is characterized in that the beam is an X-ray beam.

In the present invention, distribution of a trace element is allowed to be obtained from a detection result of X-rays generated on a sample. Thus, time and effort necessary for obtaining element distribution are reduced and element distribution covering as much as possible the elements contained in the sample is obtained rapidly. Such excellent effects are provided by the present invention.

The above and further objects and features of the invention will more fully be apparent from the following detailed description with accompanying drawings.

DETAILED DESCRIPTION

The present invention is described below in detail with reference to the drawings illustrating embodiments thereof.

Figure 1:
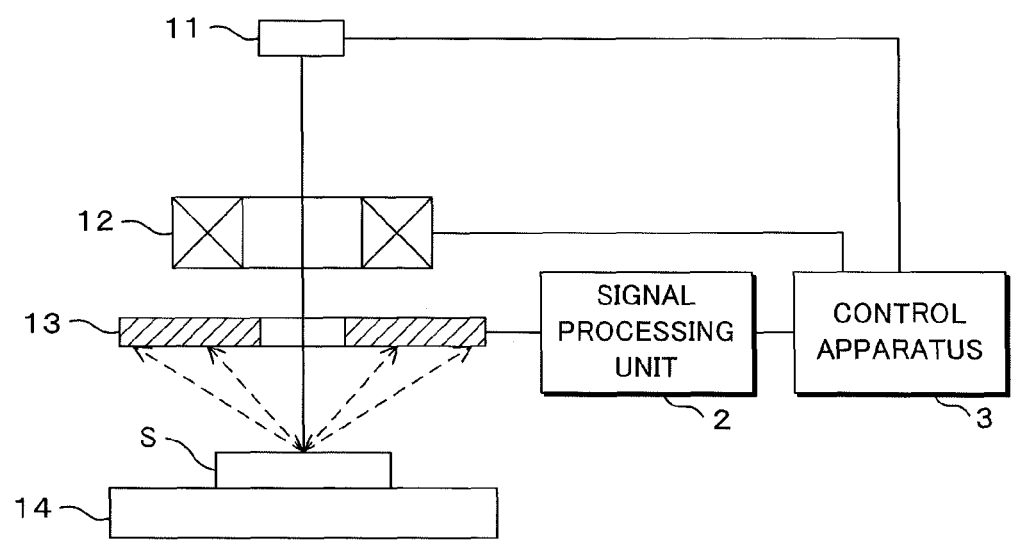
FIG. 1 is a block diagram illustrating a configuration of an X-ray analyzer.

FIG. 1 is a block diagram illustrating the configuration of an X-ray analyzer. The X-ray analyzer includes: an electron gun 11 projecting an electron beam (beam) onto a sample S; an electron lens system 12; and a sample stage 14 on which the sample S is placed. The electron lens system 12 includes a scanning coil changing the direction of the electron beam and corresponds to scanning means of the present invention.

The electron gun 11 and the electron lens system 12 are connected to a control apparatus 3 controlling the entirety of the X-ray analyzer. Here, in FIG. 1, the sample S having a planar shape is illustrated. However, the X-ray analyzer is allowed to measure a sample having another shape such as a spherical shape.

An X-ray detector 13 is arranged between the electron lens system 12 and the sample stages 14. The X-ray detector 13 is formed in a shape having a hole through which the electron beam passes. Further, the X-ray detector 13 configured by including an SDD (Silicon Drift Detector) as an X-ray sensor. For example, the X-ray detector 13 has a configuration that a plurality of SDDs are mounted on a board in which a hole is formed and then the plurality of SDDs are arranged around the hole. FIG. 1 illustrates a cross section of the X-ray detector 13. The X-ray detector 13 is arranged at a position that the electron beam passes through the hole, and arranged in a manner that the axis of the electron beam is perpendicular to the X-ray incident surface. Further, a cooling device (not illustrated) such as a Peltier device is attached to the X-ray detector 13. In a state that the sample S is placed on the sample stage 14, the X-ray detector 13 is arranged in front of the surface of the sample S onto which the electron beam is projected. In accordance with a control signal from the control apparatus 3, the electron gun 11 emits an electron beam and then the electron lens system 12 sets forth the direction of the electron beam, so that the electron beam pass through the hole of the X-ray detector 13 and then are projected onto the sample S on the sample stage 14. On the sample S, characteristic X-rays are generated at a portion onto which the electron beam is projected. Then, the generated characteristic X-rays are detected by the X-ray detector 13. In FIG. 1, the electron beam is indicated by a solid-line arrow and the characteristic X-rays are indicated by dashed-line arrows. The X-ray detector 13 outputs a signal proportional to the energy of the detected characteristic X-ray. In the configuration of the X-ray analyzer, at least the electron gun 11, the electron lens system 12, the X-ray detector 13, and the sample stage 14 are placed in a vacuum chamber (not illustrated). The vacuum chamber is constructed from a material shielding electron rays and X-rays. Further, the inside of the vacuum chamber is kept at a vacuum during the operation of the X-ray analyzer.

A signal processing unit 2 processing the outputted signal is connected to the X-ray detector 13. The signal processing unit 2 receives the signals outputted by the X-ray detector 13 and then performs the processing of counting the signals of each value and then acquiring the relation between the energy and the number of counts of the characteristic X-rays detected by the X-ray detector 13, that is, a spectrum of the characteristic X-rays. The signal processing unit 2 is connected to the control apparatus 3. The electron lens system 12 sequentially changes the direction of the electron beam so that the electron beam is projected onto the sample S in a manner of scanning the sample S. When the electron beam scan the sample S, the electron beam is sequentially projected onto each portion within the scan area of the sample S. In association with the scan of the sample S with the electron beam, characteristic X-rays generated at each portion on the sample S are sequentially detected by the X-ray detector 13. The signal processing unit 2 sequentially performs signal processing so as to sequentially generate a spectrum of characteristic X-rays generated at each portion on the sample S. The signal processing unit 2 sequentially outputs to the control apparatus 3 the data of the generated spectrum of the characteristic X-rays.

Figure 2:
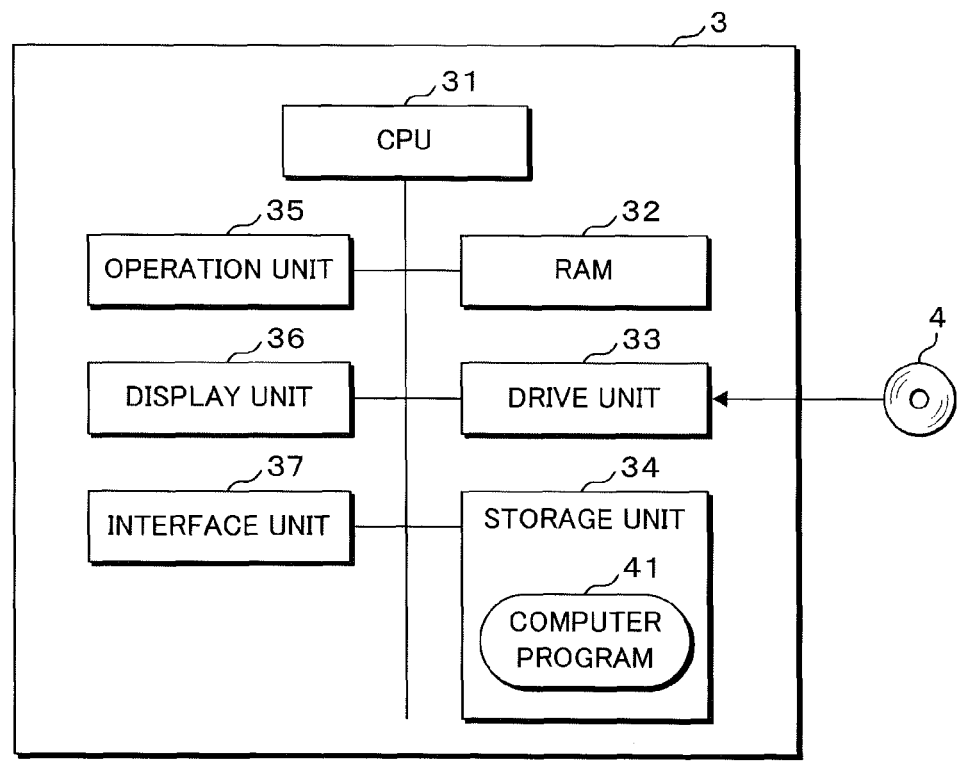
FIG. 2 is a block diagram illustrating an internal configuration of a control apparatus.

FIG. 2 is a block diagram illustrating the internal configuration of the control apparatus 3. The control apparatus 3 is configured by employing a computer such as a personal computer. The control apparatus 3 includes: a CPU (Central Processing Unit) 31 performing arithmetic operation; a RAM (Random Access Memory) 32 storing temporary data generated in association with the arithmetic operation; a drive unit 33 reading information from a recording medium 4 such as an optical disc; and a nonvolatile storage unit 34 such as a hard disk. Further, the control apparatus 3 includes: an operation unit 35 such as a keyboard and a mouse receiving operation by a user; a display unit 36 such as a liquid crystal display; and an interface unit 37. The interface unit 37 is connected to the electron gun 11, the electron lens system 12, and the signal processing unit 2. The CPU 31 causes the drive unit 33 to read a computer program 41 recorded on the recording medium 4 and then causes the storage unit 34 to store the read-out computer program 41. The computer program 41 is loaded from the storage unit 34 to the RAM 32 when necessary. Then, in accordance with the loaded computer program 41, the CPU 31 executes the processing necessary for the X-ray analyzer. Here, the computer program 41 may be downloaded from the outside of the control apparatus 3. The control apparatus 3 receives through the interface unit 37 the data of the spectrum of characteristic X-rays outputted from the signal processing unit 2, and then stores the data into the storage unit 34. Further, the control apparatus 3 controls the operation of the electron lens system 12 connected to the interface unit 37.

Figure 3:
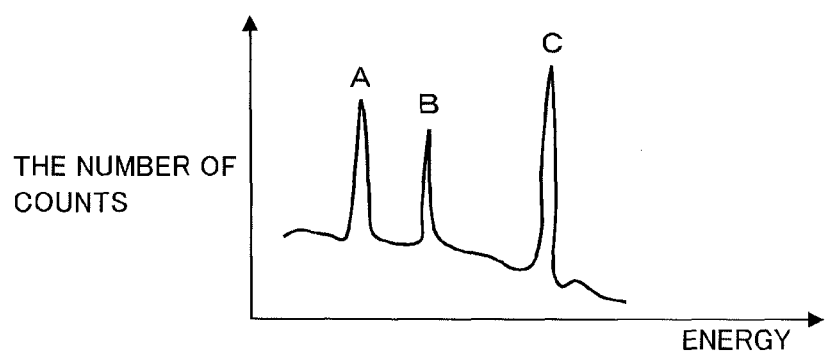
FIG. 3 is a characteristics diagram indicating an example of a spectrum of characteristic X-rays.

An element contained in the sample S is identified from the spectrum of characteristic X-rays obtained on the sample S. FIG. 3 is a characteristics diagram indicating an example of the spectrum of characteristic X-rays. The horizontal axis in the figure indicates the energy and the vertical axis indicates the number of counts of characteristic X-rays for each energy. The spectrum illustrated in FIG. 3 includes peaks indicated by A, B, and C. The energy of each peak caused by various elements is known in advance. Thus, when the energy of the peak caused by each element is compared with the energy of a peak included in the spectrum, an element corresponding to the peak included in the spectrum is identified. The identified element is contained in the sample S. The peak indicated by A is premised to be caused by element A, the peak indicated by B is premised to be caused by element B, and the peak indicated by C is premised to be caused by element C.

Figure 4:
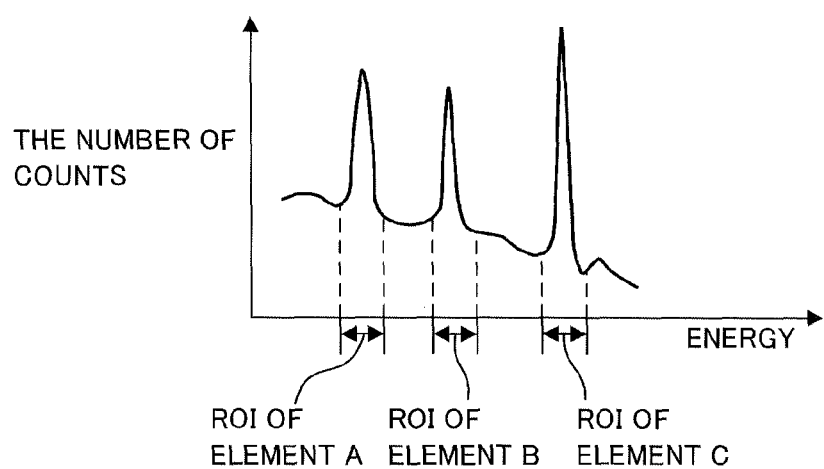
FIG. 4 is a characteristics diagram illustrating an example of an ROI.

After the element has been identified, setting of an ROI is allowed. FIG. 4 is a characteristics diagram illustrating an example of an ROI. Among the energies of the characteristic X-rays, a range of energy where the intensity of the peak of element A is not less than the intensity of the background signal is set up as the ROI of element A. The ROI of element B and the ROI of element C are set up similarly. Here, the energy range set up as the ROI may be set forth by another method like the half-value width of each peak is set up as the energy width of the ROI.

Figure 5:
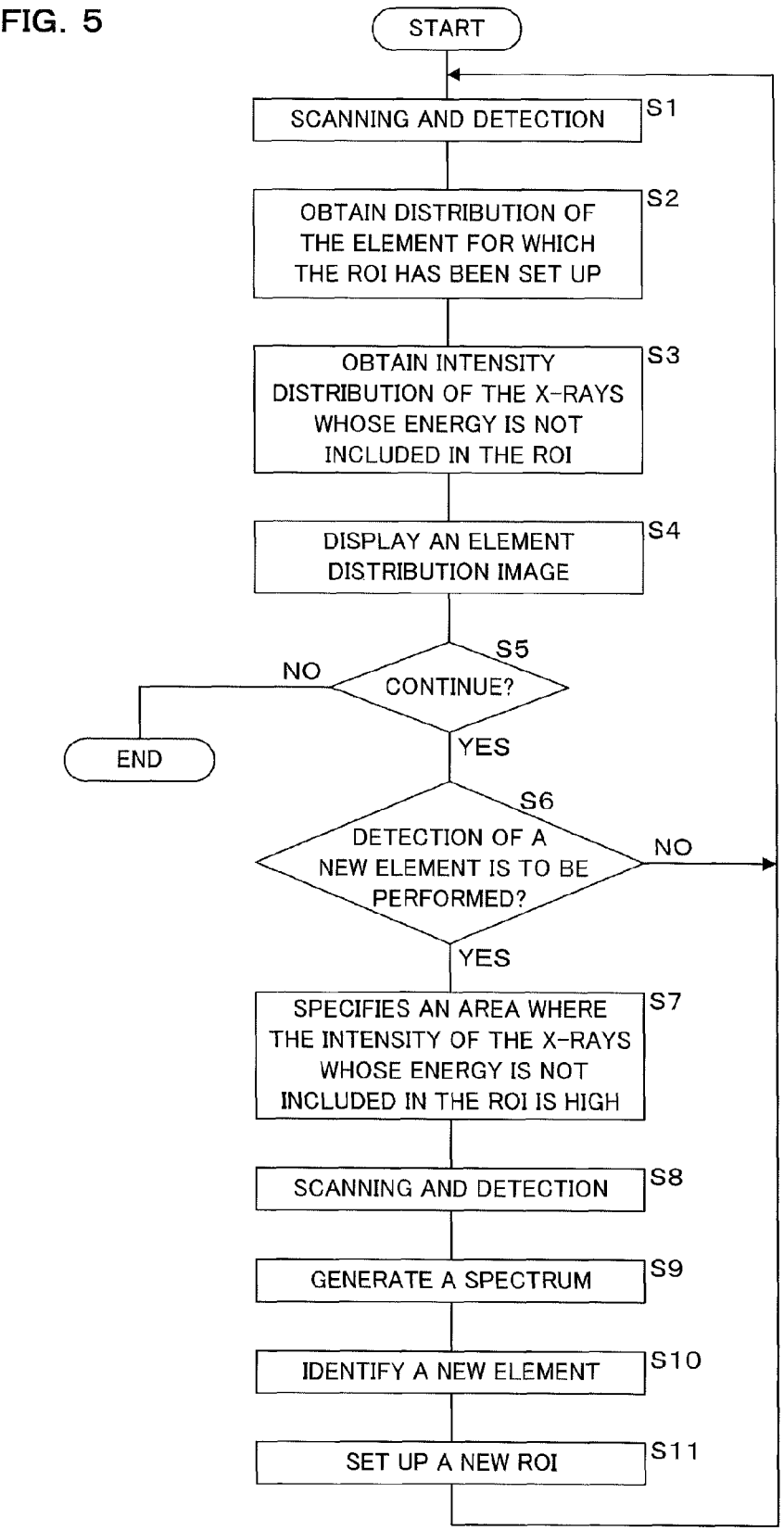
FIG. 5 is a flow chart illustrating a procedure of processing executed by an X-ray analyzer.

FIG. 5 is a flow chart illustrating a procedure of the processing executed by the X-ray analyzer. The user identifies in advance an element contained in the sample S from the spectrum of characteristic X-rays obtained in advance. Then, the user operates the operation unit 35 so as to set up in advance an ROI corresponding to the identified element. The data indicating the ROI set up in advance is stored in the storage unit 34. However, even in a state that the ROI is not set up in advance, the X-ray analyzer is allowed to execute the following processing. In response to a trigger such as an instruction generated by operation of the user and then received through the operation unit 35, the CPU 31 transmits a control signal from the interface unit 37 to the electron gun 11 and the electron lens system 12 so that the X-ray analyzer starts the processing. The electron gun 11 emits an electron beam and then the electron lens system 12 adjusts the direction of the electron beam in accordance with the control from the control apparatus 3, so that the sample S is scanned with the electron beam and then the X-ray detector 13 detects the characteristic X-rays (S1). The electron lens system 12 two dimensionally scans an area of set-forth size on the sample S. The X-ray detector 13 outputs, to the signal processing unit 2, signals corresponding to the energies of the detected characteristic X-rays. With the progress of the scanning, the signal processing unit 2 sequentially generates a spectrum of characteristic X-rays generated at each portion on the sample S. Further, the CPU 31 reads from the storage unit 34 the data indicating the already set-up ROI and then outputs the data from the interface unit 37 to the signal processing unit 2. Then, the signal processing unit 2 receives the data indicating the ROI.

From the generated spectrum of the characteristic X-rays, the signal processing unit 2 acquires the number of counts of characteristic X-rays whose energy is included in the ROI indicated by the received data, then establishes correspondence between the acquired number of counts and each portion on the sample S where the characteristic X-rays have been generated, and thereby obtains distribution of the element for which the ROI has been set up (S2). In a case that ROIs of a plurality of elements are set up, by using the number of counts of the characteristic X-rays whose energy is included in each ROI, the signal processing unit 2 obtains element distribution for each element. The signal processing unit 2 outputs the data of the obtained element distribution to the control apparatus 3. The control apparatus 3 receives the data of element distribution through the interface unit 37. Then, the CPU 31 stores the data of element distribution into the storage unit 34. Here, in a case that completely no ROI is set up, the processing of step S2 is skipped. Then, from the spectrum of the characteristic X-rays, the signal processing unit 2 acquires the number of counts of characteristic X-rays whose energy is not included in the already set-up ROI, then establishes correspondence between the acquired the number of counts and each portion on the sample S where the characteristic X-rays have been generated, and thereby obtains intensity distribution of the characteristic X-rays whose energy is not included in the already set-up ROI (S3).

Figure 6A:
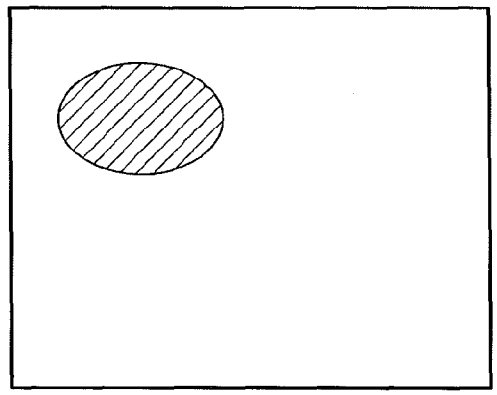
FIG. 6A is a schematic diagram illustrating an example of an element distribution image.
Figure 6B:
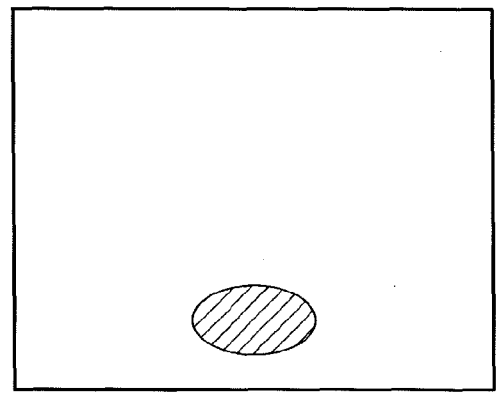
FIG. 6B is a schematic diagram illustrating an example of an element distribution image.
Figure 6C:
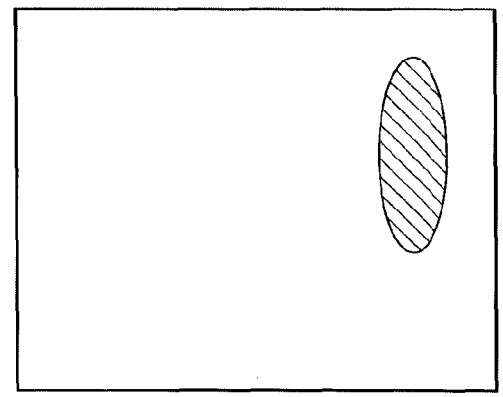
FIG. 6C is a schematic diagram illustrating an example of an element distribution image.

Then, the CPU 31 causes the display unit 36 to displays an element distribution image representing the element distribution generated at step S2 (S4). The element distribution image is an image in which the amount of each element contained at each portion on the sample S is represented. FIGS. 6A, 6B and 6C are schematic diagrams each illustrating an example of the element distribution image. FIG. 6A illustrates the distribution of element A, FIG. 6B illustrates the distribution of element B, and FIG. 6C illustrates the distribution of element C. Each hatched portion in the figures indicates a portion where the intensity of the characteristic X-rays caused by each element on the sample S is high, that is, an area where the content of each element on the sample S is high. At step S4, an element distribution image illustrated in FIG. 6A, 6B, or 6C is displayed on the display unit 36. Here, in FIGS. 6A, 6B, and 6C, the plurality of element distribution images are illustrated individually. However, the X-ray analyzer may be in a mode that an element distribution image in which the distribution of the plurality of elements are represented as one image is displayed. Here, in a case that completely no ROI is set up, the CPU 31 does not display the element distribution image on the display unit 36.

Then, in accordance with given conditions, for example, whether an instruction of termination inputted to by operation of the user has been received through the operation unit 35, whether distribution of elements has been obtained in a number set forth in advance, and whether a given time set forth in advance has been elapsed, the CPU 31 determines whether the processing is to be continued (S5). When the processing is not to be continued (S5: NO), the CPU 31 terminates the processing. When the processing is to be continued (S5: YES), in accordance with given conditions, for example, whether distributions of elements of a predetermined number has been obtained, the CPU 31 determines whether detection of a new element in addition to the already identified elements is to be performed (S6). When it is determined that detection of a new element is not to be performed (S6: NO), the CPU 31 returns the processing to step S1 so as to repeat scanning.

Figure 7:
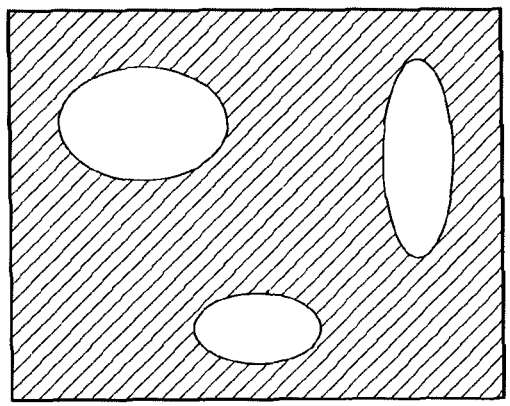
FIG. 7 is a schematic diagram illustrating an example of intensity distribution of characteristic X-rays whose energy is not included in an ROI.

When it is determined that detection of a new element is to be performed (S6: YES), then, the signal processing unit 2 specifies an area on the sample S corresponding to the portion where the intensity of the characteristic X-rays is higher than a predetermined intensity in the intensity distribution obtained at step S3 (S7). The employed predetermined intensity may be a constant value set forth in advance or alternatively a value obtained by averaging the intensity of the characteristic X-rays included in the intensity distribution. FIG. 7 is a schematic diagram illustrating an example of the intensity distribution of characteristic X-rays whose energy is not included in the ROI. The hatched portion in the figure indicates a portion where the intensity of the characteristic X-rays is high and corresponds to the area specified at step S7. In the example illustrated in FIG. 7, the intensity of the characteristic X-rays is low in the portions corresponding to the areas where the content of element A illustrated in FIG. 6A, element B illustrated in FIG. 6B, and element C illustrated in FIG. 6C is high. In the areas specified at step S7, the intensity of the characteristic X-rays not caused by the already identified elements is high. Thus, a probability is present that an element different from the already identified elements is contained.

Then, the CPU 31 causes the electron gun 11 and the electron lens system 12 to operate so as to scan the sample S with the electron beam. Then, the X-ray detector 13 detects the characteristic X-rays (S8). The signal processing unit 2 sequentially generates spectra of the characteristic X-rays detected by the X-ray detector 13, then integrates the spectra of the characteristic X-rays generated from each portion of the area specified at step S7, and thereby generates a spectrum of the characteristic X-rays generated in the specified area on the sample S at a stage of termination of the scan (S9). Here, the spectrum may be generated by averaging the plurality of spectra of the characteristics X-rays. The signal processing unit 2 outputs the data of the spectrum to the control apparatus 3. The control apparatus 3 receives the data of the spectrum through the interface unit 37. Then, the CPU 31 stores the data of the spectrum into the storage unit 34. The generated spectrum of the characteristic X-rays is a spectrum corresponding to the content of elements contained in the area of the sample S specified at step S7.

Figure 8:
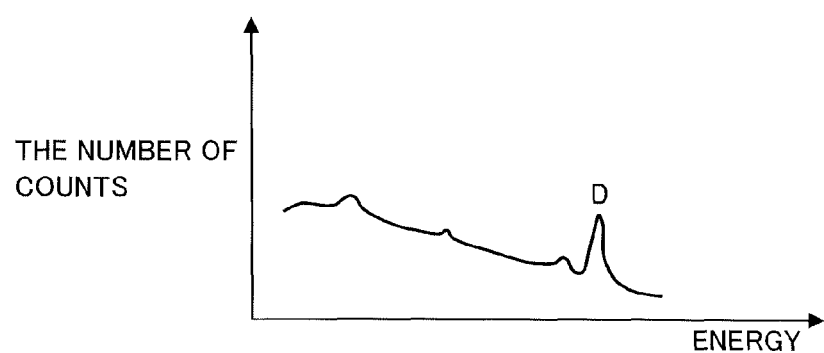
FIG. 8 is a characteristics diagram illustrating an example of a spectrum of characteristic X-rays generated at step S9.

FIG. 8 is a characteristics diagram illustrating an example of the spectrum of characteristic X-rays generated at step S9. Characteristic X-rays from the area where the content of the already identified elements is high is not included. Thus, the intensities of the peaks caused by element A, element B, and element C are small. Further, the spectrum is a spectrum of characteristic X-rays from an area having a possibility that an element different from the already identified elements is contained. Thus, when an element different from the already identified elements is contained in the sample S, a peak caused by the element is included in the spectrum. The peak caused by the element different from the already identified elements appears as a relatively large peak. In FIG. 8, a peak not related to any of element A, element B, and element C is indicated by D. The peak indicated by D is premised to be a peak caused by element D.

Then, on the basis of the peak included in the generated spectrum of the characteristic X-rays, the CPU 31 performs the processing of identifying a new element contained in the sample S (S10). The storage unit 34 stores in advance the data recording the energies of characteristic X-rays corresponding to various elements. At step S10, the CPU 31 detects a peak included in the spectrum of the characteristic X-rays and then specifies the energy of the detected peak. The CPU 31 compares the specified energy with the energies of characteristic X-rays corresponding to various elements and thereby identifies the element. For example, element D causing the peak indicated by D in FIG. 8 is identified.

Then, the CPU 31 sets up a new ROI which is an energy range of characteristic X-rays corresponding to the newly identified element (S11). Specifically, the CPU 31 sets as an ROI an energy range that includes the peak in the spectrum used for identifying the element. Here, the energy range set up as the ROI may be set forth by another method like the half-value width of each peak is set up as the energy width of the ROI. At step S11, for example, the ROI of element D is set up.

Figure 9:
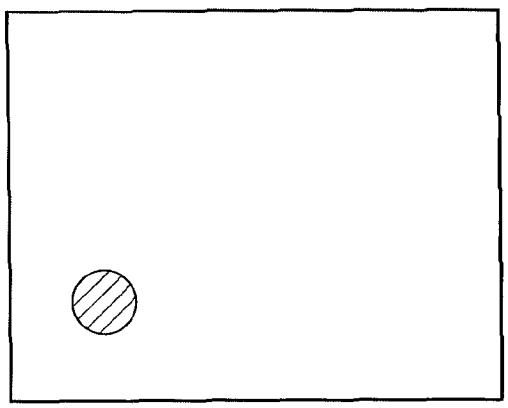
FIG. 9 is a schematic diagram illustrating an example of a new element distribution image.

Then, the CPU 31 returns the processing to step 51. At that time, the CPU 31 outputs the data indicating the ROI set up at step S11, from the interface unit 37 to the signal processing unit 2. Then, the signal processing unit 2 receives the data indicating the ROI. After that, at step S2, on the basis of the newly set-up ROI, element distribution of the newly identified element in the sample S is obtained. Then, at step S4, the new element distribution image is displayed on the display unit 36. FIG. 9 is a schematic diagram illustrating an example of the new element distribution image. In FIG. 9, the distribution of element D different from any of element A, element B, and element C is illustrated. The hatched portion in the figure indicates an area where the content of element D in the sample S is high. The distribution of element D having a lower content and inhomogeneously distributed in a smaller area than element A, element B, and element C is obtained.

When the processing of steps S1 to S11 is repeated, elements contained in the sample S are identified sequentially. Then, element distribution images of the identified element is sequentially displayed on the display unit 36. The user is allowed to check the displayed element distribution image. At a stage that an appropriately number of elements have been identified and then the element distribution images have been displayed, the user is allowed to operate the operation unit 35 so as to terminate the processing of the X-ray analyzer. Further, generation of the spectrum of characteristic X-rays and obtaining element distribution are executed by the signal processing unit 2 which is hardware. Thus, rapid display of the element distribution image is achieved easily.

As described above, in the X-ray analyzer of the present invention, element distribution in the sample S is obtained by using an ROI, then an area on the sample S where the intensity of characteristic X-rays whose energy is not included in already set-up ROIs is high is specified, then a spectrum of the characteristic X-rays obtained from the specified area is generated, and thereby an element for which an ROI is not set up is identified from the generated spectrum. In the specified area, the intensity of characteristic X-rays not caused by the elements for which an ROI is already set up is high. Thus, it is possible that a new element is contained. The area where characteristic X-rays are to be acquired is limited to an area where a new element is able to be contained. Thus, the ratio of the area where a new element is contained to the area where characteristic X-rays are to be acquired becomes relatively large. Accordingly, in the spectrum of the characteristic X-rays, the peak caused by a new element becomes relatively large. That is, the peak of a trace element buried in the background or among other peaks in the spectrum of characteristic X-rays obtained from the entirety of the sample S becomes a detectable peak. Thus, identification of the trace element becomes easy. Further, the X-ray analyzer sets an ROI corresponding to the identified element and then obtains element distribution. Thus, even when the identified trace element is inhomogeneously distributed, distribution of the trace element is allowed to be obtained. Further, the X-ray analyzer repeats specification of an area, generation of a spectrum of characteristic X-rays, identification of an element, setting of an ROI, scan of the sample, and obtaining element distribution. Unintended omission of setting of an ROI is avoided and hence the elements including trace elements contained in the sample S are allowed to be covered as much as possible. Since distribution of trace elements is allowed to be obtained from the detection result of characteristic X-rays, time and effort become unnecessary that have been necessary for obtaining distribution of trace elements on the basis of an image other than an element distribution image. Thus, in the present invention, element distribution covering as much as possible the elements contained in the sample S is allowed to be obtained easily and rapidly.

Here, in the processing executed by the X-ray analyzer, at step S9, the CPU 31 may generate a spectrum of characteristic X-rays within an energy range excluding the already set-up ROIs. The spectrum in this case does not include the number of counts of the characteristic X-rays corresponding to the already set-up ROIs and hence does not include the peaks caused by the already identified elements. Thus, when an element different from the already identified elements is contained in the sample S, the peak caused by the element appears more clearly in the spectrum.

Further, the present embodiment has been described for a mode that scan of the sample S is repeated in the processing of steps S1 to S11. However, the X-ray analyzer may be in a mode that the number of times of scanning the sample S is reduced. For example, the X-ray analyzer may be in a mode that the data obtained when the sample S is scanned at step S1 is stored into the storage unit 34 and then the processing at and after step S2 is executed on the basis of the stored data. In this mode, without executing the scan at step S8, on the basis of the data stored in the storage unit 34, the X-ray analyzer executes the processing of generation of a spectrum, identification of an element, obtaining element distribution, and the like. Also in this mode, the X-ray analyzer is allowed to easily and rapidly obtain element distribution covering as much as possible the elements contained in the sample S.

Further, the present embodiment has been described for a mode that the X-ray analyzer displays an element distribution image. However, the X-ray analyzer may be in a mode that the element distribution image is not displayed. For example, the X-ray analyzer may be in a mode that the element distribution image is not displayed and that information indicating the situation of progress of the processing such as the names of identified elements and the number of identified elements is displayed on the display unit 36.

Further, the present embodiment has been described for a mode that the X-ray detector 13 is arranged at a position intersecting with the axis of an electron beam. However, the X-ray analyzer may be in a mode that the X-ray detector 13 is arranged at another position. For example, the X-ray analyzer may be in a mode that the X-ray detector 13 is arranged on the side of the electron lens system 12. Further, the present embodiment has been described for a mode of energy dispersive X-ray analyzer type in which characteristic X-rays are detected with being separated depending on the energy. However, the X-ray analyzer may be in a mode of wavelength dispersive X-ray analyzer in which characteristic X-rays are detected with being separated depending on the wavelength. In this mode, the X-ray analyzer generates a spectrum in which correspondence is established between the wavelength and the number of counts of the characteristic X-rays, and further performs the processing of setting as an ROI the wavelength range of the characteristic X-rays corresponding to a particular element. Further, in the present embodiment, the X-ray detector 13 has been premised to be a semiconductor detector employing an SDD. However, the X-ray detector 13 may be a semiconductor detector other than an SDD and may be a detector other than a semiconductor detector.

Further, the signal processing unit 2 may be in a mode of executing a part of the processing of the control apparatus 3 described in the present embodiment. Further, the control apparatus 3 may be in a mode of executing a part of the processing of the signal processing unit 2 describing in the present embodiment. Further, the X-ray analyzer may be in a mode that the signal processing unit 2 and the control apparatus 3 are integrated with each other. Further, the X-ray analyzer according to the present embodiment may be in a mode of being incorporated in an SEM (scanning electron microscope) or a TEM (transmission electron microscope). In this mode, for the SEM or TEM application, the X-ray analyzer includes: a detector detecting electrons such as backscattered electrons, secondary electrons, and transmission electrons; and a signal processor processing a signal from the detector. Further, in this mode, at the time that an area on the sample S corresponding to a portion where the intensity of characteristic X-rays whose energy is not included in the ROI is high is specified at step S7, the X-ray analyzer may perform the processing of specifying the area on the basis of the contrast in the intensity of backscattered electrons, secondary electrons, or transmission electrons.

Further, the present embodiment has been described for a mode that the sample S is scanned by using an electron beam. However, the X-ray analyzer may be in a mode that the sample S is scanned by using another beam. For example, the X-ray analyzer may be in a mode that the sample S is scanned by using an X-ray beam. In this mode, the X-ray analyzer includes an X-ray source in place of the electron gun 11, does not include the electron lens system 12, and includes means of moving the sample stage 14 in a horizontal direction. With projecting an X-ray beam onto the sample S, the X-ray analyzer moves the sample stage 14 so as to move the X-ray projection position and thereby scans the sample S with the X-ray beam. The X-ray detector 13 detects X-ray fluorescence generated in the sample S. Further, the X-ray analyzer may be in a mode that the sample S is scanned by using a charged-particle beam. Also in these modes, the X-ray analyzer is allowed to obtain element distribution covering as much as possible the elements contained in the sample S.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. An X-ray analyzer, comprising:
a scanning unit for scanning a sample with a beam;

an X-ray detector for detecting X-rays generated on the sample by the scanning;

an element distribution obtaining unit for, from the detection result of the X-rays generated in an area on the sample scanned with the beam, obtaining intensity distribution of the X-rays whose energy or wavelength is included in a range of energy or wavelength set up in correspondence to an element contained in the sample and thereby obtaining distribution of the element;

an intensity distribution acquiring unit for acquiring intensity distribution of X-rays whose energy or wavelength is not included in the range;

an area specifying unit for specifying an area on the sample corresponding to a portion where the intensity of X-rays is not less than a predetermined intensity in the intensity distribution;

a spectrum generating unit for generating a spectrum of X-rays generated in the specified area on the sample;

an element identification unit for identifying an element contained in the sample on the basis of a peak included in the generated spectrum; and a setting unit for setting a range of energy or wavelength of X-rays corresponding to the identified element, wherein the element distribution obtaining unit obtains distribution of the element identified by the element identification means, in accordance with the range set by the setting means.

2. The X-ray analyzer according to claim 1, further comprising a display unit for displaying an image representing the distribution of the element at each time that the element distribution obtaining unit obtains the distribution.

3. The X-ray analyzer according to claim 1, wherein the scanning unit scans the area specified by the area specifying unit with the beam, the X-ray detector detects X-rays generated on the area scanned with the beam, and the spectrum generating unit generates a spectrum of X-rays generated on the area on the basis of the detection result of the X-rays by the X-ray detector.

4. The X-ray analyzer according to claim 1, wherein the spectrum generating unit generates a spectrum of X-rays whose energy or wavelength is not included in the already set range of energy or wavelength.

5. The X-ray analyzer according to claim 1, wherein the element distribution obtaining unit, the intensity distribution acquiring unit, the area specifying unit, the spectrum generating unit, the element identification unit and the setting unit operates repetitively until distributions of elements of a predetermined number are obtained.

6. The X-ray analyzer according to claim 1, wherein the beam is an electron beam.

7. The X-ray analyzer according to claim 1, wherein the beam is an X-ray beam.

8. The X-ray analyzer according to claim 1, wherein the area specifying unit specifies a portion, in the intensity distribution acquired by the intensity distribution acquiring unit, where the intensity of X-rays whose energy or wavelength is not included in the already set range is not less than a predetermined intensity and specifies an area on the sample corresponding to the specified portion.

9. The X-ray analyzer according to claim 1, wherein the predetermined intensity is a constant value.

10. The X-ray analyzer according to claim 1, wherein the predetermined intensity is a value obtained by averaging the intensity of X-rays included in the intensity distribution acquired by the intensity distribution acquiring unit.

11. The X-ray analyzer according to claim 6, further comprising a detector for detecting backscattered electrons, wherein the area specifying unit specifies the area on the basis of the contrast in the intensity of backscattered electrons.

* * * * *